United States Patent [19]

Koester et al.

[11] Patent Number: 4,793,850
[45] Date of Patent: Dec. 27, 1988

[54] EVAPORATION INHIBITOR COMPOSITIONS

[75] Inventors: Josef Koester, Duesseldorf; Karl Schmid, Mettmann; Konrad Albrecht, Kelkheim; Paul Bittner, Kriftel; Fritz Keim, Hofheim, all of Fed. Rep. of Germany

[73] Assignees: Henkel Kommanditgesellschaft auf Aktien, Duesseldorf; Hoechst Aktiengesellschaft, Frankfurt am Main, both of Fed. Rep. of Germany

[21] Appl. No.: 798,210

[22] Filed: Nov. 14, 1985

[30] Foreign Application Priority Data

Mar. 2, 1985 [DE] Fed. Rep. of Germany ....... 3507380

[51] Int. Cl.$^4$ ............................................. A01N 25/02
[52] U.S. Cl. .................... 71/79; 71/DIG. 1; 106/271; 47/DIG. 11
[58] Field of Search ............................ 71/DIG. 1, 79; 47/DIG. 11; 106/271; 514/772

[56] References Cited

U.S. PATENT DOCUMENTS

| | | | |
|---|---|---|---|
| 2,284,970 | 6/1942 | Avery | 47/58 |
| 2,580,653 | 1/1952 | Bridgeman | 71/2.6 |
| 2,976,210 | 3/1961 | Cosby et al. | 167/42 |
| 3,154,402 | 10/1964 | Salvesen et al. | 71/DIG. 1 |
| 3,791,839 | 2/1974 | Cushman et al. | 106/268 |
| 3,873,689 | 3/1975 | Frensch et al. | 424/78 |
| 4,329,390 | 5/1982 | Danner | 106/271 |

FOREIGN PATENT DOCUMENTS

| | | |
|---|---|---|
| 1937634 | 2/1970 | Fed. Rep. of Germany . |
| 2415843 | 10/1975 | Fed. Rep. of Germany . |
| 2451490 | 5/1976 | Fed. Rep. of Germany . |
| 2053631 | 4/1971 | France . |
| 214518 | 10/1984 | German Democratic Rep. . |
| 214519 | 10/1984 | German Democratic Rep. . |
| 215227 | 11/1984 | German Democratic Rep. . |
| 74/6734 | 10/1974 | South Africa . |
| 699196 | 3/1951 | United Kingdom . |
| 897644 | 9/1959 | United Kingdom . |
| 926862 | 6/1961 | United Kingdom . |
| 1072045 | 11/1963 | United Kingdom . |
| 1062457 | 8/1964 | United Kingdom . |
| 1136082 | 1/1966 | United Kingdom . |
| 1274921 | 7/1969 | United Kingdom . |
| 1272408 | 7/1969 | United Kingdom . |
| 1307313 | 4/1970 | United Kingdom . |
| 1367183 | 8/1972 | United Kingdom . |

Primary Examiner—Catherine L. Mills
Attorney, Agent, or Firm—Ernest E. Szoke; Henry E. Millson, Jr.; Real J. Grandmaison

[57] ABSTRACT

An evaporation inhibitor composition which consists essentially of:
A. from about 15 to about 50% by weight of a wax mixture containing at least about 5% by weight, based on the wax mixture, of a wax component having an acid number of from about 10 to about 95 mg KOH/g wax;
B. from about 4 to about 20% by weight of at least one nonionic and/or anionic emulsifier;
C. from about 19.5 to about 81% by weight of water and/or at least one organic solvent selected from the group consisting of hydrocarbons, esters, and ketones having a boiling point of from about 70° to about 280° C.

19 Claims, No Drawings

EVAPORATION INHIBITOR COMPOSITIONS

BACKGROUND OF THE INVENTION

1. Field of the Invention

The present invention relates to evaporation inhibitors, and to methods for using such iniibitors to reduce the evaporation of water from spray mixtures of agricultural chemicals.

2. Description of Related Art

Agricultural chemicals are widely used nowadays to safeguard the growth and yield of crops, and are usually applied by airplane to cover large areas under cultivation. To minimize the costs involved, every effort is made to keep the quantites of water required for diluting the commercial concentrates as small as possible and to apply high concentrations of active compounds in small amounts. Today, quantities of 5–50 liters/ha are applied by the low-volume (LV) method using known commercial products, such as wettable powders (WP), suspended concentrates (SC) or solvent-containing emulsifiable concentrates (EC) which are normally sprayed in suspension in 300–600 liters of water/ha using ground appliances.

The smaller the quantities of spray mixture applied per unit area, the finer the droplets applied have to be to obtain satisfactory coverage of the crops. This plus the high concentration of the spray mixtures has hitherto created the main obstacle to application of the low-volume method, particularly under sub-tropical and tropical climatic conditions, namely, the water evaporates too quickly due to the large surface area of the fine droplets, so that increased drifting losses can occur.

In addition to drifting losses, damage may even be caused to adjacent crops, depending on the plant treatment agent used. Accordingly, controlled application from aircraft is difficult; and damage to the environment or losses of harvest may have to be accepted.

In addition, heavy foaming can occur during preparation of the spray mixture with the greatly reduced quantities of water, because the dispersants and wetting agents in the wettable powders or concentrated dispersions are then present in correspondingly higher concentrations. The product foams out of the spray tanks unless the filling level is greatly reduced.

The above spray mixtures of agricultural chemicals are prepared from commercial concentrates by dispersion or emulsification in the desired quantity of water. The concentrates are either self-emulsifying solutions in an organic solvent (EC) or wettable powders (WP) or suspended concentrates (SC).

The agricultural chemicals used may be insecticides, fungicides, virucides, herbicides, acaricides, dessicants, growth regulators, ripening accelerators, repellents, pheromones, leaf fertilizers, defoliants, etc. In addition, the concentrates optionally contain dispersants, emulsifiers, wetting agents, defoamers, stickers, carriers and pigments for obtaining a marking effect.

The object of the present invention is to reduce the evaporation of water in the application by the low-volume method of agricultural chemicals in the form of spray mixtures. Measures in that direction are the subject of German Application No. 22 05 590, although the mineral-oil-based evaporation inhibitors claimed therein are not sufficiently effective under sub-tropical and tropical climatic conditions. In addition, it is known from U.S. Pat. No. 3,791,839 that the release of water from living plants, particularly during growth in dry climates, can be reduced by applying to the surface of the plants an aqueous emulsion which, in addition to paraffin wax and emulsifier, contains vaseline-like hydrocarbons (petrolatum) as a required ingredient. However, the function of these emulsions is not to reduce the evaporation of spray mixtures of plant protection agents during spraying by the low-volume method.

DESCRIPTION OF THE INVENTION

Other than in the operating examples, or where otherwise indicated, all numbers expressing quantities of ingredients or reaction conditions used herein are to be understood as modified in all instances by the term "about".

The present invention relates to evaporation inhibitors (EI) for spray mixtures containing one or more agricultural chemicals applied by the LV method in the form of a wax-containing aqueous dispersion or self-emulsifying solution in an organic solvent, wherein the inhibitors contain:

from 15 to 50% by weight of a wax mixture containing at least 5% by weight, based on the wax mixture, of a wax component having an acid number of from 10 to 95 mg KOH/g wax, from 4 to 20% by weight of at least one non-ionic and/or anionic emulsifier, from 19.5 to 81% by weight of water and/or one or more organic solvents from the group of hydrocarbons, esters and ketones having boiling points of from 70° to 280° C., from 0 to 5.5% by weight of auxiliaries, from 0 to 5.0% by weight of a amine or an alkali metal hydroxide.

The wax mixture preferably has one of the following compositions, with the percentages by weight being based on the total weight of the wax mixture:

Mixture (A)

from 60 to 95% by weight of paraffin wax and/or microcrystalline paraffin wax having a setting point of from 40° to 70° C.

from 5 to 40% by weight of oxidized polyethylene wax having a dropping point of from 95° to 140° C. and an acid number of from 10 to 95 mg KOH/g wax

Mixture (B)

from 60 to 95% by weight of paraffin wax and/or microcrystalline paraffin wax having a setting point of from 40° to 70° C.

from 5 to 40% by weight of wax containing ester bonds and having a dropping point of from 75° to 100° C. and an acid number of from 10 to 95 mg KOH/g wax

Mixture (C)

from 20 to 50% by weight of paraffin wax having a setting point of from 30° to 50° C.

from 50 to 80% by weight of oxidized paraffin wax having a setting point of from 60° to 90° C. and an acid number of from 10 to 95 mg KOH/g wax The present invention also relates to a process for reducing the evaporation of water from spray mixtures of agricultural chemicals during application by the LV method, wherein from 1 to 15% by weight and preferably from 5 to 10% by weight of an evaporation inhibitor of the invention is added to the spray mixtures adjusted to the "in-use" concentration.

The inhibitors of the invention can be present in the form of solutions of the wax and emulsifier constituents in the organic solvent. Solutions such as these are temperature-stable and storable and, when stirred into water or spray mixtures adjusted to the "in-use" concentration, form dispersions which show high thermal stability under normal practical conditions.

However, the inhibitors cccording to the invention are preferably used in the form of concentrated aqueous dispersions because, in that form, they are easier to incorporate in the spray mixtures due to the absence or substantial absence of solvent. The dispersions are prepared, for example, by melting the constituents to be dispersed (wax mixture, emulsifiers, optionally organic solvents) together and then adding the desired amount of water and, optionally, other auxiliaries. In the case of relatively high melting wax mixtures, it is best to stir the molten wax mixture into the water heated to 80°–100° C., followed by rapid cooling. The dispersion shows high temperature stability and high stability in storage, enabling it to be used even under sub-tropical and tropical climatic conditions.

The preferred inhibitors of the invention are used in the form of aqueous dispersions having the following compositions:

from 15 to 40% by weight of wax mixture (A), (B) or (C) described above,
from 4 to 20% by weight and preferably from 4 to 14% by weight of one or more nonionic emulsifiers,
from 0 to 10% by weight and preferably from 1 to 7% by weight of one or more anionic emulsifiers, the nonionic emulsifiers making up at least 50% by weight of the emulsifiers,
from 29.5 to 81% by weight of water,
from 0 to 10% by weight of xylene or cyclohexanone or a petroleum fraction having a boiling point of from 145° to 210° C. or an ester having a boiling point of from 70° to 280° C.,
from 0 to 5% by weight of one or more hydrotropes,
from 0 to 0.5% by weight of one or more inorganic salts,
from 0 to 5.0% by weight of an amine or an alkali metal hydroxide.

The aqueous dispersions are particularly suitable for use in spray mixtures based on solvent-containing concentrates (EC) and wettable powders (WP). The ready-to-use spray mixtures are prepared simply by stirring the aqueous dispersion into the spray mixtures adjusted to the "in-use" concentration. The inhibitor is added to the spray mixture in a quantity of from 1 to 15% by weight and preferably in a quantity of from 5 to 10% by weight.

In the treatment of large areas, the spray mixtures are generally applied by airplane in the form of a very fine spray mist, although portable or mobile appliances may be used for smaller areas.

By virtue of the presence in them of wax mixtures specifically adapted to the particular "in-use" conditions, the claimed evaporation inhibitors greatly inhibit the evaporation of water from the droplets of spray mist during application. In this way, the droplets largely retain their weight, resulting in an increased rate of fall and less drifting under the effect of wind. This leads to a better effect of the plant treatment agents and, hence, to increases in crop yield. Moreover, the quantities of active ingredients can also be reduced. In addition, the fact that the quantity of liquid is maintained in the droplets of spray mixture avoids undesirable concentrations of the active ingredients, providing for slow release which can have a positive effect on the phytotoxicity of the agents used.

In addition, the wax present in the inhibitors has a foam-damping effect, thus preventing excessive foaming during preparation of the spray mixtures and their introduction into tanks and the like.

Compositions containing petrolatum such as those disclosed in U.S. Pat. No. 3,791,839 are not useful for the purposes of the present invention, i.e., the necessary reduction of evaporation of water from spray mixtures of agricultural chemicals is not achieved during spraying when petrolatum is a component of the compositions. In addition, compositions as disclosed in U.S. Pat. No. 3,791,839 are not generally suitable for mixing with emulsion spray mixtures of agricultural chemicals due to interference with the stability of the emulsions, especially in hot climates. Furthermore, the presence of petrolatum adversely affects the storage stability of the evaporation inhibitors of the invention, particularly during extended storage in hot climates.

The following products are preferably used in wax mixtures (A), (B) and (C) above:

(a) Natural or synthetic paraffin waxes and microcrystalline paraffin waxes having setting points in the above-mentioned ranges, for example ozocerite, paraffin waxes from the distillation of petroleum, microparaffins from crude oil residues or synthetic paraffins obtained by the Fischer-Tropsch synthesis. The paraffin waxes consist essentially of linear or branched-chain hydrocarbons of relatively high molecular weight.

(b) Oxidized polyethylene waxes having dropping points of from 95° to 140° C., of the type obtained by partial oxidation of polyethylenes. The acid number is preferably in the range from 10 to 70 mg KOH/g wax.

(c) Oxidized paraffin waxes having setting points of from 60° to 90° C. and an acid number of from 10 to 95 mg KOH/g wax, of the type obtained by partial oxidation of paraffins.

(d) Waxes containing ester bonds preferably emanating from natural sources, such as for example montan waxes in crude or refined form, vegetable waxes, such as carnauba or candelilla wax, or insect waxes, such as shellac wax. The ester waxes have dropping points of from 75° to 100° C. and are optionally used in prehydrolyzed form with an acid number of from 10 to 95 mg KOH/g wax.

The emulsifiers used are preferably nonionic surfactants or surfactant mixtures, including for example the sorbitan esters of higher fatty acids and long-chain alkyl glycosides and also alkylene oxide adducts with higher, $C_{10}$-$C_{24}$ linear monofunctional and polyfunctional alcohols, alkylphenols, long-chain carboxylic acids, carboxylic acid amides and hydroxy fatty acids as well as with fatty acid glycerol or sorbitan esters and long-chain alkyl glycosides. It is preferred to use the adducts of from 2 to 50 moles of ethylene oxide with long-chain, $C_{12}$-$C_{18}$ preferably primary alcohols and fatty acids. To improve the temperature stability of the aqueous inhibitor dispersions, it is advisable to combine two or more alkylene oxide adducts differing in their degree of alkoxylation with one another. A mixture of ethylene oxide adducts with $C_{12}$-$C_{18}$ fatty alcohols or alkylphenols consisting of from 10 to 40% by weight of adducts containing from 1 to 4 moles of ethylene oxide,
from 25 to 70% by weight of adducts containing from 4 to 10 moles of ethylene oxide, from 5 to 35% by weight of adducts containing from 10 to 50 moles of ethylene oxide has proved to be particularly effective. The above percentages by weight are based on the total weight of the adduct mixture.

The dispersions can be further stabilized by replacing part of the nonionic emulsifiers by anionic emulsifiers. Suitable anionic emulsifers are the alkali metal, ammonium, amine and alkaline earth metal salts of long-chain alkyl sulfates, sulfonates, and phosphoric acid partial esters. Particularly suitable anionic emulsifiers are the salt of sulfuric acid semiesters or phosphoric acid partial esters of linear alcohols or alkylphenols containing from 12 to 18 carbon atoms or polyglycol monoalkylethers containing from 12 to 18 carbon atoms in the alkyl group and also olefin sulfonates, ester sulfonates and alkane sulfonates containing from 12 to 20 carbon atoms, alkylbenzene sulfonates containing from 6 to 16 carbon atoms in the alkyl groups, sulfonates of polyglycol monoalkylethers and salts of polyglycol monoalkylether carboxylic acids containing from 12 to 18 carbon atoms in the alkyl groups. Of these surfactants, alkylbenzene sulfonates and alkane sulfonates are preferably used.

The emulsifiers are used in a total quantity of from 4 to 10% by weight, and preferably from 4 to 14% by weight, based on the inhibitor dispersion or solution. Where anionic emulsifiers are present, they preferably make up at least 0.5% by weight and more especially at least 1.0% by weight of the inhibitor as a whole. The nonionic emulsifiers should preferably make up at least 50% by weight of the total quantity of emulsifiers.

The organic solvents optionally present in the inhibitor formulations are liquid hydrocarbons, esters or ketones having boiling points of from 70° to 280° C., for example light mineral oils, toluene, liquid fatty acid methylesters and the like. Preferred solvents are xylene, cyclohexanone, and petroleum fractions boiling at temperatures in the range of from 145° to 210° C.

Other auxiliaries which can be added as desired in a total quantity of up to 5.5% by weight, more especially to the inhibitor dispersions, include dyes, viscosity regulators, foam regulators, preservatives, inorganic salts, hydrotropes and other dispersion aids. Of particular importance to the dispersions in this respect are hydrotropes and salts which influence the structure of the aqueous component of the dispersion and thus enable viscosity and degree of dispersion to be regulated. Preferred hydrotropes are non-surface-active salts of aromatic sulfonic acids, such as sodium cumene sulfonates, and of sulfuric acid semiesters with $C_6$-$C_{10}$ alcohols. The hydrotropes need only be used in quantities of up to 5% by weight. Suitable inorganic salts, which may be added in quantities of up to 0.5% by weight, are in particular the sodium or potassium salts of mineral acids. In addition, small quantities of up to 5% by weight of amines or alkali metal hydroxides are preferably used for adjusting the pH of the dispersion and for neutralizing the oxidized polyethylene or paraffin waxes or ester waxes containing acidic groups. Alkanolamines, such as diethanolamine, morpholine, sodium or potassium hydroxide are particularly suitable.

The type of agricultural chemicals used in the spray mixtures is not critical to the use of the evaporation inhibitors (EI) according to the invention. For example, the inhibitors may be used for applying the following plant protection agents (the list of which is not intended to limit the invention in any way):

Pyrethroids, such as deltamethrin, cypermethrin, fenpropathrin, cyfluthrin, fenvalerate, permethrin; (thio)phosphoric acid esters, such as triazophos, parathion-methyl, dimethoat, heptebophos, pyrazophos, profenofos, sulprofos, dialifos, chlorpyrifos, anilofos; carbamates, such as BPMC, carbaryl, propoxur, methomyl, carbofuran, phenmedipham, desmedipham, pririmicarb; chlorinated hydrocarbons, such as camphechlor, dicofol; chitin synthesis inhibitors, such as diflurbenzuron, trifluron, teflubenzuron (CME 134) or chlorfluazuron (IKI 7899); the agents endosulfan, amitraz, clofentezine, phosetyl AL, prochloraz; herbicides of the phenoxy or heteroaryloxy phenoxy propionic acid derivative type, such as diclofopmethyl, fenoxaprop-ethyl, fluazifop-butyl, haloxyfopethoxyethyl (Dowco 453), quinofop-ethyl; urea derivatives, such as diuron, iospropturon, linuron, monolinuron, chlortoluron, sulfonyl ureas, such as chlorsulfuron, sulfometuron; triazines such as ametryn, atrazine, simazine; halogenated phenoxy acetic acid or propionic acid derivatives, such as MCPA, dichlorprop, 2,4,5-T, mecoprop, 2,4-D, esters or salts thereof; aniline derivatives, such as butachlor, propanil, benzoylpropethyl, alachlor, metolachlor; nitrophenol derivatives, such as binapacryl or dinosebacetat, nitroaniline derivatives, such as trifluralin or pendimethalin; benzothiadiazines, such as bentazone; the agents ioxynil, bromoxynil, metamitron, glufosinate or salts thereof, bialophos or salts thereof, glyphosate or salts thereof, triazole derivatives, such as triadimefon; the fungicides metal axyl, iprodione, fenarimol, triforine, propiconazol, tridemorph, pyracarbolid; agents containing heavy metals, such as maneb, sineb, triphenyl tin compounds, such as fentin-acetate or fentin hydroxide, azocyclotin, cyhexatin, copperoxy chloride; plant growth regulators, such as mepiquatchloride or chlormequatchloride or similar salts, ancymidol, tetcyclasis or mefluidid. Further information on these treatment agents may be found in CH.R. Worthing, S. B. Walker, The Pesticide Manual, 7th Ed., British Crop Protection Council, London, 1985.

The invention will be illustrated but not limited by the following examples.

I. Formulation Examples for EI

All quantities in percent by weight.

Dp.=dropping point (as determined by DGF method III 3)

Sp.=setting point (as determined by DGF method III 4a)

A No.=acid number (as determined by DGF method IV 2)

EO=ethylene oxide.

EXAMPLE 1

(type: wax mixture (A))

20.0% paraffin wax, Sp. 50° to 54° C.

10.0% oxidized polyethylene wax, Dp. 100° to 105° C., A No. 23 to 28

0.5% diethanolamine 2.0% $C_{12}$-$C_{18}$ coconut oil fatty alcohol+2 EO 6.0% tallow fatty alcohol+6 EO 2.0% tallow fatty alcohol+12 EO 59.5% deionized water.

EXAMPLE 2

(type: wax mixture (A))

27.0% paraffin wax, Sp. 50° to 54° C.

3.0% oxidized polyethylene wax, Dp. 108° to 111° C., A No. 20 to 3
0.1% diethanolamine
2.0% $C_{12}$-$C_{18}$ coconut oil fatty alcohol+2 EO
6.0% tallow fatty alcohol+6 EO
2.0% tallow fatty alcohol+12 EO
59.9% deionized water.

EXAMPLE 3

(type: wax mixture (A))
25.0% paraffin wax, Sp. 50° to 54° C.
2.5% oxidized polyethylene wax, Dp. 100° to 105° C., A No. 23 to 28
2.5% oleyl alcohol (iodine number 50-55)+2 EO
4.2% tallow fatty alcohol+6 EO
2.5% tallow fatty alcohol+12 EO
0.1% diethanolamine
2.0% sodium cumene sulfonate (40%)
2.7% octanol/decanol sulfate, sodium salt
58.5% deionized water.

EXAMPLE 4

(type: wax mixture (B))
27.0% paraffin wax, Sp. 50° to 53° C.
3.0% ester wax (Montan wax), Dp. 82° to 88° C., A No. 25 to 35
0.1% diethanolamine
2.0% $C_{12}$-$C_{18}$ coconut oil fatty alcohol+2 EO
6.0% tallow fatty alcohol+6 EO
2.0% tallow fatty alcohol+12 EO
59.9% deionized water.

EXAMPLE 5

(type: wax mixture (C))
14.0% paraffin wax, Sp. 30° to 35° C.
16.0% oxidized paraffin wax, Sp. 65° to 70° C., A No. 30 to 35
3.5% diethanolamine
2.0% $C_{12}$-$C_{18}$ coconut oil fatty alcohol+2 EO
6.0% tallow fatty alcohol+6 EO
2.0% tallow fatty alcohol+12 EO
56.5% deionized water.

EXAMPLE 6

(type: wax mixture (A))
25.0% paraffin wax, Sp. 50° to 52° C.
2.5% oxidized polyethylene wax, Dp. 108° to 111° C., A No. 20 to 30
2.5% oleyl alcohol+2 EO
4.2% tallow alcohol+6 EO
2.5% tallow alcohol+12 EO
0.1% diethanolamine
2.0% $C_{16}$-$C_{18}$ alkane sulfonate, Na salt, 60%
1.5% sodium cumene sulfonate, 40%
0.2% preservative
59.7% water.

EXAMPLE 7

(type: wax mixture (A))
27.0% paraffin wax, Sp. 50° to 54° C.
3.0% oxidized polyethylene wax, Dp. 108° to 111° C., A No. 20 to 30
10.0% dodecyl benzene sulfonate, Ca salt, 70% in xylene
5.0% nonionic surfactant of $C_8$-$C_{10}$/$C_{16}$-$C_{18}$ fatty alcohol mixture+2 PO+11 EO
55.0% xylene.

II. Testing the evaporation-inhibiting effect using test mixtures free from active substances (AS)

The following test mixtures were used for testing the evaporation-inhibiting effect:

| EC type: | 10 g of AS-free concentrate of 8 g of xylene and 2 g of emulsifier mixture (1.2 g of nonylphenol + 15 EO, 0.8 g of dodecylbenzene sulfonate, Ca salt, 70%) were emulsified in 80 g of water, followed by the addition of quantities of 10 g of the inhibitors of Examples 2 to 4 and 1 to 5 |
|---|---|
| blank value: | 10 g of concentrate without inhibitor in 90 g of water |

To test the inhibition of evaporation, quantities of 50 g of the spray mixtures were introduced into a plane bottomed glass dish (diameter 120 mm, height 20 mm) and the evaporation as a function of time produced by a steady stream of air was determined by weighing out at various temperatures. The results are shown in Tables 1 and 2.

TABLE 1

Tests at 25° C.
Test mixture EC-type Evaporation loss in % by weight

|  | ½ h | 1 h | 2 h | 3 h | 4 h | 24 h |
|---|---|---|---|---|---|---|
| Blank value | 9.5 | 15.9 | 27.0 | 37.5 | 48.3 | 97.9 |
| Example 2 | 0.5 | 0.5 | 0.5 | 0.8 | 1.0 | 2.7 |
| Example 3 | 0.7 | 0.8 | 1.0 | 1.1 | 1.3 | 3.1 |
| Example 4 | 0.6 | 0.9 | 1.4 | 1.5 | 1.9 | 3.9 |

TABLE 2

Tests at 50° C.
Test mixture EC-type Evaporation loss in % by weight

|  | ½ h | 1 h | 1½ h | 2 h | 2½ h | 3 h |
|---|---|---|---|---|---|---|
| Blank value | 37 | 71 | 92 | — | — | — |
| Example 1 | 17 | 19 | 21 | 23 | 24 | 25 |
| Example 2 | 5 | 7 | 10 | 13 | 15 | 17 |
| Example 3 | 6 | 9 | 12 | 15 | 21 | 26 |
| Example 4 | 11 | 16 | 20 | 24 | 27 | 30 |
| Example 5 | 9 | 17 | 22 | 25 | 29 | 35 |

III. Testing the evaporation-inhibiting effect on test mixtures containing active substances 10% test mixtures were prepared from three standard commercial plant protection agent concentrates. The inhibitor (EI) of example 3 was then added to the test mixtures in quantities of 0%, 5% and 10%.

To measure evaporation behaior, quantities of 50 ul of these spray mixtures were introduced into a cylindrical aluminium dish (diameter 6.5 mm, height 1.5 mm). The evaporation as a function of time produced by a steady stream of air (40 h) at 50° C. was measured by means of a thermobalance, the weight of the sample being continuously recorded by a recorder. The results are shown in Table 3 below:

TABLE 3

| Active substance concentrate | Inhibitor (% by weight) | Weight of the sample in mg after ... mins. | | | | | |
|---|---|---|---|---|---|---|---|
| | | 0 | 30 | 60 | 90 | 120 | 150 |
| Hostathion ® | 0% | 50 | 8 | 3 | 3 | 3 | 3 |

TABLE 3-continued

| Active substance concentrate | Inhibitor (% by weight) | Weight of the sample in mg after ... mins. | | | | | |
|---|---|---|---|---|---|---|---|
| | | 0 | 30 | 60 | 90 | 120 | 150 |
| | 5% | 50 | 41 | 35 | 30 | 25 | 20 |
| | 10% | 50 | 43 | 41 | 40 | 39 | 38 |
| Afugan ® | 0% | 50 | 9 | 2 | 2 | 2 | 2 |
| | 5% | 50 | 41 | 35 | 30 | 26 | 23 |
| | 10% | 50 | 42 | 40 | 38 | 37 | 36 |
| Illoxan ® | 0% | 50 | 9 | 3 | 3 | 3 | 3 |
| | 5% | 50 | 40 | 36 | 31 | 26 | 21 |
| | 10% | 50 | 41 | 36 | 32 | 29 | 26 |
| Water | 0% | 50 | 10 | 0 | 0 | 0 | 0 |

Hostathion ® (HOECHST AG) contains the insecticide 1-phenyl-3-(O,O—diethylthionophosphoryl)-1,2,4-triazole, emulsifiers and xylene.
Afugan ® (HOECHST AG) contains the fungicide 2-(O,O—diethyl-thionophosphoryl)-5-methyl-6-carbethoxy-pyrazolo-(1,5-a)-pyrimidine, emulsifiers and xylene.
Illoxan ® (HOECHST AG) contains the herbicide 2-(4-(2',4'-dichlorophenoxy)-phenoxy)-propionic acid methylester, emulsifiers, xylene and cyclohexanone.

Illoxan ® (HOECHST AG) contains the herbicide 2-(4-(2,4-dichlorophenoxy)-phenoxy)-propionic acid methylester, emulsifiers, xylene and cyclohexanone.

IV. Testing the evaporation-inhibiting effect directly on droplets of the test mixtures Hemi-spherical droplets with a volume of approx. 0.01 ul were formed at the tip of a 1 ul Hamilton syringe arranged horizontally under a microscope by carefully pushing in the plunger. In order to measure evaporation, the size of the droplets was measured after certain time intervals using a graduated scale incorporated in the eyepiece and the droplet volume calculated therefrom. The tests were carried out at 23° C./55% relative air humidity.

The three spray mixtures tested contained 10% by weight of Hostaquick ®, HOECHST AG (which contains the insecticide 6-chlorobicyclo(3,2,0)hepta-2,6-dien-6-yl dimethylphosphate, emulsifiers and xylene), the inhibitor of Example 3 and standard water having a hardness of 342 ppm. The test results are shown in Table 4 below in the form of average values from five tests.

TABLE 4

| Inhibitor content | Droplet volume in 1/1000 ul after ... seconds | | | | | | | |
|---|---|---|---|---|---|---|---|---|
| | 0 | 20 | 40 | 60 | 80 | 100 | 120 | 140 |
| 0% | 11 | 2.8 | 0.0 | — | — | — | — | — |
| 2.5% | 11 | 5.3 | 3.2 | 2.1 | 1.3 | 0.5 | 0.0 | — |
| 5% | 11 | 7.0 | 6.1 | 5.4 | 4.6 | 3.9 | 3.1 | 2.4 |
| Water | 11 | 2.0 | 0.0 | — | — | — | — | — |

What is claimed is:

1. An evaporation inhibitor composition consisting of:
   A. from about 15 to about 50% by weight of a wax mixture containing at least about 5% by weight, based on the wax mixture, of a wax component having an acid number of from about 10 to about 95 mg KOH/g wax; said wax mixture being selected from one of the following:
      a. from about 60 to about 95% by weight of paraffin wax and/or microcrystalline paraffin wax having a setting point of from about 40° to about 70° C., and from about 5 to about 40% by weight of oxidized polyethylene wax having a dropping point of from about 95° to about 140° C. and an acid number of from about 10 to about 95 mg KOH/g wax;
      b. from about 60 to about 95% by weight of paraffin wax and/or microcrystalline paraffin wax having a setting point of from about 40° to about 70° C., and from about 5 to about 40% by weight of wax containing ester bonds and having a dropping point of from about 75° to about 100° C. and an acid number of from about 10 to about 95 mg KOH/g wax; and
      c. from about 20 to about 50% by weight of paraffin wax having a setting point of from about 30° to about 50° C., and from about 50 to about 80% by weight of oxidized paraffin wax having a setting point of from about 60° to about 90° C. and an acid number of from about 10 to about 95 mg KOH/g wax;
   B. from about 4 to about 20% by weight of at least one nonionic and/or anionic emulsifier; and
   C. from about 19.5 to about 81% by weight of water and/or at least one organic solvent selected from the group consisting of hydrocarbons, esters, and ketones having a boiling point of from about 70° to about 280° C.

2. A composition in accordance with claim 1 wherein up to 5% by weight of an amine or an alkali metal hydroxide is also present therein.

3. A composition in accordance with claim 1 wherein up to 5.5% by weight of one or more of a dye, a viscosity regulator, a foam regulator, a preservative, an inorganic salt, and a hydrotrope is also present therein.

4. A composition in accordance with claim 2 wherein up to 5.5% by weight of one or more of a dye, a viscosity regulator, a foam regulator, a preservative, an inorganic salt, and a hydrotrope is also present therein.

5. A composition in accordance with claim 1 wherein the composition consists essentially of:
   A. from about 15 to about 40% by weight of a., b., or c.;
   B. an emulsifier which is
      a. from about 4 to about 20% by weight of at least one nonionic emulsifier, and
      b. from 0 to about 10% by weight of at least one anionic emulsifier, wherein the nonionic emulsifier makes up at least 50% by weight of component B;
   C. from about 29.5 to about 81% by weight of water and from 0 to about 10% by weight of the at least one organic solvent;
   D. from 0 to about 5% by weight of at least one hydrotrope;
   E. from 0 to about 0.5% by weight of at least one inorganic salt; and
   F. from 0 to about 5.0% by weight of an amine or an alkali metal hydroxide.

6. A composition in accordance with claim 6 wherein component B.b. is present in from about 1 to about 7% by weight.

7. A composition in accordance with claim 5 wherein component B.a. is present in from about 4 to about 14% by weight and component B.b. is present in from about 1 to about 7% by weight.

8. A composition in accordance with claim 1 wherein the at least one nonionic emulsifier of component B is at least one of a sorbitan ester of a higher fatty acid or a long-chain alkyl glycoside, and an alkylene oxide adduct with a higher, $C_{10}$-$C_{24}$ linear monofunctional or polyfunctional alcohol, an alkylphenol, a long-chain carboxylic acid, a carboxylic acid amide, a hydroxy fatty acid, or a fatty acid glycerol, or sorbitan ester or a long-chain alkyl glycoside.

9. A composition in accordance with claim 8 wherein the at least one nonionic emulsifier is at least one of an adduct of from 2 to 50 moles of ethylene oxide with a $C_{12}$–$C_{18}$ long-chain primary alcohol or fatty acid.

10. A composition in accordance with claim 1 wherein at least one nonionic emulsifier in component B. is a mixture of ethylene oxide adducts with $C_{12}$–$C_{18}$ fatty alcohols or an alkylphenol having
from about 10 to about 40% by weight of adducts containing from 1 to 4 moles of ethylene oxide,
from about 25 to about 70% by weight of adducts containing from 4 to 10 moles of ethylene oxide, and
from about 5 to about 35% by weight of adducts containing from 10 to 50 moles of ethylene oxide.

11. A composition in accordance with claim 1 wherein the anionic emulsifier in component B is at least one of a salt of a sulfuric acid semiester, a phosphoric acid partial ester of a linear alcohol or an alkylphenol containing from 12 to 18 carbon atoms or a polyglycol monoalkylether containing from 12 to 18 carbon atoms in the alkyl group, an olefin sulfonate, an ester sulfonate, and an alkane sulfonate wherein such sulfonates contain from 12 to 20 carbon atoms, an alkylbenzene sulfonate containing from 6 to 16 carbon atoms in the alkyl group, a sulfonate of a polyglycol monoalkylether, and a salt of a polyglycol monoalkylether carboxylic acid containing from 12 to 18 carbon atoms in the alkyl chain.

12. A composition in accordance with claim 11 wherein the anionic emulsifier is one or more of an alkylbenzene sulfonate containing from 6 to 16 carbon atoms in the alkyl group, and an alkane sulfonate containing from 12 to 20 carbon atoms.

13. A composition in accordance with claim 1 wherein component B. is present in from about 4 to about 14% by weight.

14. An aqueous agricultural spray composition comprising at least one agriculturally active ingredient and from about 1 to about 15% by weight of an evaporation inhibitor composition of claim 1.

15. An aqueous spray composition in accordance with claim 14 wherein from about 5 to about 10% by weight of an evaporation inhibitor composition of claim 1 is present therein.

16. A method for reducing the evaporation of water from an aqueous spray mixture containing at least one agricultural chemical comprising mixing therewith an evaporation inhibitor composition consisting essentially of:
A. from about 15 to about 50% by weight of a wax mixture containing at least about 5% by weight, based on the wax mixture, of a wax component having an acid number of from about 10 to about 95 mg KOH/g wax; said wax mixture being selected from one of the following:
  a. from about 60 to about 95% by weight of paraffin wax and/or microcrystalline paraffin wax having a setting point of from about 40° to about 70° C., and from about 5 to about 40% by weight of oxidized polyethylene wax having a dropping point of from about 95° to about 140° C. and an acid number of from about 10 to about 95 mg KOH/g wax;
  b. from about 60 to about 95% by weight of paraffin wax and/or microcrystalline paraffin wax having a setting point of from about 40° to about 70° C., and from about 5 to about 40% by weight of wax containing ester bonds and having a dropping point of from about 75° to about 100° C. and an acid number of from about 10 to about 95 mg KOH/g wax; and
  c. from about 20 to about 50% by weight of paraffin wax having a setting point of from about 30° to about 50° C., and from about 50 to about 80% by weight of oxidized paraffin wax having a setting point of from about 60° to about 90° C. and an acid number of from about 10 to about 95 mg KOH/g wax;
B. from about 4 to about 20% by weight of at least one nonionic and/or anionic emulsifier;
C. from about 19.5 to about 81% by weight of water and/or at least one organic solvent selected from the group consisting of hydrocarbons, esters, and ketones having a boiling point of from about 70° to about 280° C., and spraying said aqueous mixture onto agricultural crops by the Low-Volume method in a quantity of from about 5 to about 50 liters/hectare.

17. A method in accordance with claim 16 wherein from about 1 to about 15% by weight of said evaporation inhibitor composition is present in said aqueous spray mixture.

18. An evaporation inhibitor composition consisting of:

A. from about 15 to about 50% by weight of a wax mixture containing at least about 5% by weight, based on the wax mixture, of a wax component having an acid number of from about 10 to about 95 mg KOH/g wax; said wax mixture being selected from one of the following:
  a. from about 60 to about 95% by weight of paraffin wax and/or microcrystalline paraffin wax having a setting point of from about 40° to about 70° C., and from about 5 to about 40% by weight of oxidized polyethylene wax having a dropping point of from about 95° to about 140° C. and an acid number of from about 10 to about 95 mg KOH/g wax;
  b. from about 60 to about 95% by weight of paraffin wax and/or microcrystalline paraffin wax having a setting point of from about 40° to about 70° C., and from about 5 to about 40% dropping point of from about 75° to about 100° C. and an acid number of from about 10 to about 95 mg KOH/g wax; and
  c. from about 20 to about 50% by weight of paraffin wax having a setting point of from about 30° to about 50° C., and from about 50 to about 80% by weight of oxidized paraffin wax having a setting point of from about 60° to about 90° C. and an acid number of from about 10 to about 95 mg KOH/g wax;

B. an emulsifier which is
  a. from about 40 to about 20% by weight of at least one nonionic emulsifier, and
  b. from 0 to about 10% by weight of at least one anionic emulsifier, wherein the nonionic emulsifier makes up at least 50% by weight of component B; said anionic emulsifier in component B is at least one of a salt of a sulfuric acid semiester, a phosphoric acid partial ester of a linear alcohol or an alkylphenol containing from 12 to 18 carbon atoms or a polyglycol monoalkylether containing from 12 to 18 carbon atoms in the alkyl group, an olefin sulfonate, and ester sulfonate, or an alkane sulfonate wherein such sulfonates contain from 12 to 20 carbon atoms, an alkylbenzene sulfonate containing from 6 to 16 carbon atoms in the alkyl groups, a sulfonate of a polyglycol monoalkylether, and a salt of a polyglycol monoalkylether carboxylic acid containing from 12 to 18 carbon atoms in the alkyl chain, and C. frmm about 19.5 to about 81% by weight of water and/or at least one organic solvent selected from the group consisting of hydrocarbons, esters, and ketones having a boiling point of from about 70° to about 280° C.

19. An evaporation inhibitor composition consisting of:

A. from about 15 to about 50% by weight of a wax mixture containing at least about 5% by weight, based on the wax mixture, of a wax component having an acid number of from about 10 to about 95 mg KOH/g wax; said wax mixture being selected from one of the following:
  a. from about 60 to about 95% by weight of paraffin wax and/or microcrystalline paraffin wax having a setting point of from about 40° to about 70° C., and from about 5 to about 40% by weight of oxidized polyethylene wax having a dropping point of from about 95° to about 140° C. and an acid number of from about 10 to about 95 mg KOH/g wax;
  b. from about 60 to about 95% by weight of paraffin wax and/or microcrystalline paraffin wax having a setting point of from about 40° to about 70° C., and from about 5 to about 40% by weight of wax containing ester bonds and having a dropping point of from about 75° to about 100° C. and an acid number of from about 10 to about 95 mg KOH/g wax; and
  c. from about 20 to about 50% by weight of paraffin wax having a setting point of from about 30° to about 50° C., and from about 50 to about 80% by weight of oxidized paraffin wax having a setting point of from about 60° to about 90° C. and an acid number of from about 10 to about 95 mg KOH/g wax;

B. from about 4 to about 20% by weight of at least one nonionic and/or anionic emulsifier; wherein said nonionic emulsifier is a mixture of ethylene oxide adducts with $C_{12}$-$C_{18}$ fatty alcohols or an alkylphenol having from about 10 to about 40% by weight of adducts containing from 1 to 4 moles of ethylene oxide, from about 25 to about 70% by weight of adducts containing from 4 to 10 moles of ethylene oxide, and from about 5 to about 35% by weight of adducts containing from 10 to 50 moles of ethylene oxide, and C. from about 19.5 to about 81% by weight of water and/or at least one organic solvent selected from the group consisting of hydrocarbons, esters, and ketones having a boiling point of from about 70° to about 280° C.

* * * * *